US008409296B2

(12) United States Patent
Knize et al.

(10) Patent No.: US 8,409,296 B2
(45) Date of Patent: Apr. 2, 2013

(54) BROW LIFT IMPLANT AND METHOD

(75) Inventors: David Knize, Colorado Springs, CO (US); Ilya S. Koyfman, Ringoes, NJ (US); J. Jenny Yuan, Branchburg, NJ (US); Michael Hoffman, Somerset, NJ (US); Donald G. Hill, Branchburg, NJ (US)

(73) Assignee: Ethicon, Inc., Somerville, NJ (US)

( * ) Notice: Subject to any disclaimer, the term of this patent is extended or adjusted under 35 U.S.C. 154(b) by 196 days.

(21) Appl. No.: 12/639,177

(22) Filed: Dec. 16, 2009

(65) Prior Publication Data

US 2011/0144750 A1 Jun. 16, 2011

(51) Int. Cl.
*A61F 2/02* (2006.01)

(52) U.S. Cl. .................................................. 623/23.72

(58) Field of Classification Search ............... 623/11.11, 623/23.72–23.76; 606/153, 154, 155, 213, 606/215, 216, 151
See application file for complete search history.

(56) References Cited

U.S. PATENT DOCUMENTS

| 5,217,494 | A | * | 6/1993 | Coggins et al. ............. 623/23.72 |
| 5,611,814 | A | * | 3/1997 | Lorenc ........................... 606/213 |
| 6,015,410 | A | | 1/2000 | Tormala et al. |
| 6,485,503 | B2 | | 11/2002 | Jacobs et al. |
| 6,908,473 | B2 | | 6/2005 | Skiba et al. |
| 7,056,331 | B2 | | 6/2006 | Kaplan et al. |
| 2001/0044637 | A1 | | 11/2001 | Jacobs et al. |
| 2002/0022861 | A1 | * | 2/2002 | Jacobs et al. ................... 606/216 |
| 2005/0240224 | A1 | | 10/2005 | Wu |
| 2005/0283256 | A1 | * | 12/2005 | Sommerich et al. ......... 623/23.74 |
| 2008/0082113 | A1 | | 4/2008 | Bishop et al. |
| 2008/0200993 | A1 | * | 8/2008 | Henderson ................... 623/23.74 |
| 2009/0030526 | A1 | * | 1/2009 | Sommerich et al. ......... 623/23.72 |
| 2009/0082791 | A1 | | 3/2009 | Schroeder |
| 2009/0198335 | A1 | | 8/2009 | Barbosa |

OTHER PUBLICATIONS

Mutaf, M., "Mesh Lift: A New Procedure for Long-Lasting Results in Brow Lift Surgery", Plastic Reconstructive Surgery (2005), 116(5), 1490-1499.
Pascali, M. "An Original Application of the Endotine Ribbon Device for Brow Lift", American Society of Plastic Surgeons, (2009) 1652-1661.
International Search Report mailed Jul. 29, 2011 for corresponding Patent Application No. PCT/US2010/059681.

* cited by examiner

*Primary Examiner* — Ryan Severson
*Assistant Examiner* — Rachel S Papeika

(57) ABSTRACT

A substantially flat implant for repositioning a patient's eyebrow that may allow for a gradient lift across the eyebrow. The implant may be geometrically non-symmetrical, and/or may have non-symmetric physical properties. The implant may include a foot portion that extends along a first longitudinal axis and has a length, and a vertical strip portion that extends outwardly from the foot portion along a second longitudinal axis. The strip portion has a length and a width that is smaller than the length of the foot. The second longitudinal axis is offset from the center of the length of the foot portion.

11 Claims, 6 Drawing Sheets

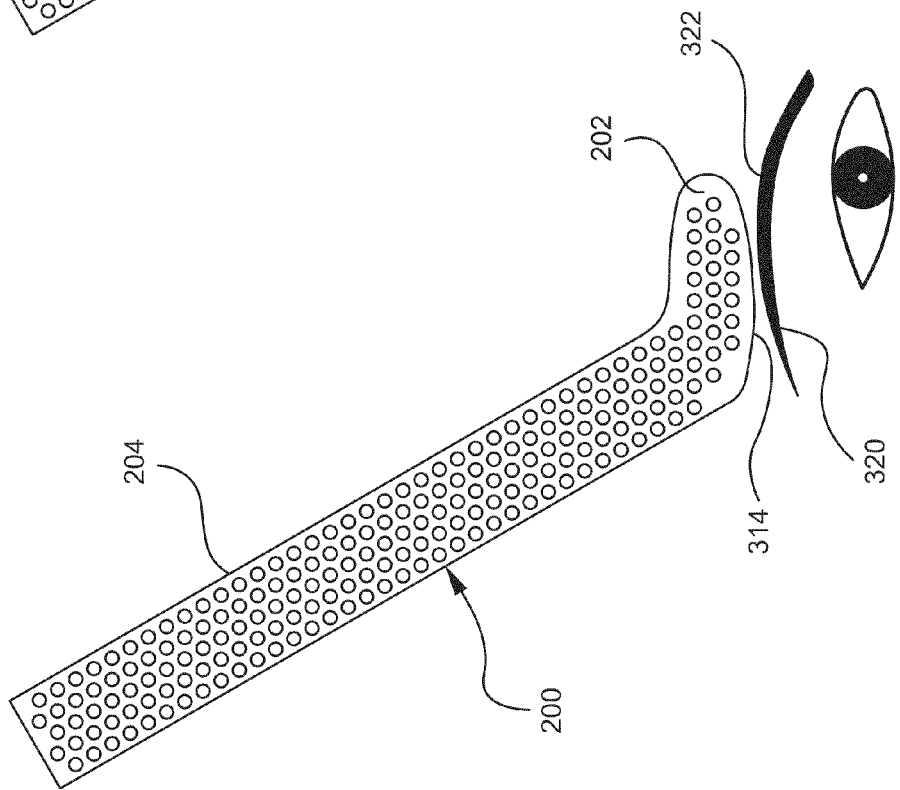
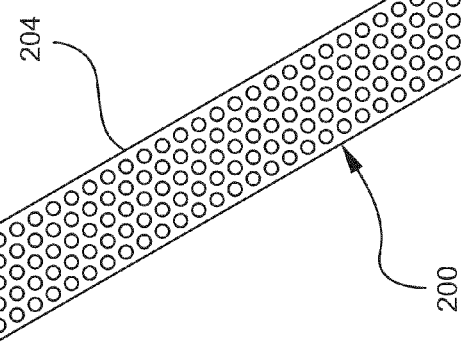
FIG. 4b
FIG. 4a

BROW LIFT IMPLANT AND METHOD

BACKGROUND OF THE INVENTION

1. Field of the Invention

The present invention relates generally to surgical implants, and more particularly to surgical implants and methods for re-positioning and/or lifting a patient's eye brow.

2. Background Discussion

Repositioning or lifting of the eyebrow is a surgical procedure typically performed to address tissue laxity or "sagging" that occurs as a result of trauma or injury, or more commonly as part of the typical aging process. In a balanced, youthful female face, the eyebrow is lower medially (toward the center of the face), and higher laterally, with a variable arch in between. In a male face, there is no distinct difference between medial and lateral aspects of the brow—the entire brow is positioned horizontally. Early signs of brow and periorbital aging include brow ptosis with a lowering of the medial and lateral hair-bearing brow and development of a vertical glabellar and horizontal forehead lines. These changes can result in alterations of facial expressions, exhibiting a tired, concerned, or even angry look. Often, there is a real or apparent excess of skin on the upper eyelid.

A variety of techniques have been used to reposition and/or reshape the brow. Most involve mobilization, repositioning, and fixation of the brow with modifications to the forehead musculature. The brow lift techniques are typically characterized as coronal, endoscopic, or limited-incision foreheadplasty techniques. The open standard coronal brow lift was for many years the only option for forehead and brow rejuvenation, and it remains today the gold standard against which other newer, less invasive techniques are measured.

In the coronal technique, a relatively long incision (7-9 cm) is typically made along the same direction as, but posterior to the frontal hairline. Alternatively the incision may be placed anterior to the frontal hairline if it is desired to shorten a long forehead. Following known dissection techniques, the forehead flap is then elevated, excess skin and tissue excised, and the wound subsequently closed. Although the technique is relatively simplistic and has wide exposure, disadvantages include the long scar, and long-term, usually permanent changes in scalp sensation due to nerve damage.

In the endoscopic technique that was introduced in the 1970's, one to three vertical frontal scalp incisions and two bilateral temporal scalp incisions are made. Through these incisions, the surgeon dissects certain portions of the tissue to transpose the forehead. The repositioned tissue is typically fixed via sutures to bone screws or the like placed in the cortical bone. This technique requires limited incisions, but requires expensive endoscopic equipment and skill in its use.

The limited-incision foreheadplasty technique is focused on the correction of the lateral portion of the brow. Two bilateral temporal scalp incisions and two upper blepharoplasty incisions are made, through which the muscles and tissue are repositioned. Although incisions are limited and endoscopic equipment is not needed, there is less visualization for dissection than with either the coronal incision or the endoscopic techniques, making familiarity with local anatomy important and requiring a skilled surgeon.

In addition to the fixation devices motioned above, devices such as barbed sutures, mesh and tined devices have also been known to be used in brow lift procedures. At least one surgeon is known to have utilized a planar, implantable polypropylene mesh in brow lift procedures. The mesh 100 is approximately 3 cm in width, and is placed under the galeal plane above the periosteum, and extends from just above the brow and up the forehead as shown in FIGS. 1 and 1a. Tissue ingrowth occurs, eventually causing the implanted mesh to serve as an artificial suspensory aponeurosis that provides stable fixation to maintain the elevated position of the eyebrow. Due to its placement under the galeal plane above the periosteum, this implant remains palpable under the forehead skin. Further, this implant and procedure does not allow a gradient brow elevation where the level of brow elevation increases from the medial toward the lateral side. Gradient brow elevation is advantageous in providing a desired, authentic result in large number of female patients.

Accordingly, there is a need for an improved implant and method for brow lift procedures.

SUMMARY OF THE INVENTION

An implant is provided for repositioning a patient's eyebrow that includes a foot portion adapted to be positioned along at least a portion of the length of the patient's eyebrow, extending along a first longitudinal axis and having a length. The implant also includes a vertical strip portion extending outwardly from the foot portion and adapted to extend upwardly across at least a portion of a patient's forehead. The vertical strip portion extends along a second longitudinal axis and has a length, and a width that is smaller than the length of the foot. The second longitudinal axis is offset from the center of the length of the foot portion, and the implant is substantially flat, having first and second opposing surfaces.

In one embodiment, the first and second longitudinal axes form an obtuse angle therebetween at the point of intersection, which preferably is greater than approximately 105 degrees, and may be approximately 105 to 125 degrees. More preferably, the angle therebetween is approximately 117 degrees.

The implant may be made of an entirely absorbable material or materials, and in one embodiment is made of an absorbable mesh.

In yet another embodiment, the implant further includes an absorbable film on the first and/or second surfaces, which may be a polydioxanone film. The polydioxanone film may have a thickness of approximately 20-200 μm, and in the alternative may have a thickness of approximately 50 μm on the vertical strip portion, and a thickness of approximately 150 μm on the foot portion.

In yet another embodiment, the implant further includes a plurality of holes therethrough.

Also provided is an implant for repositioning a patient's eyebrow, including a substantially flat, strip of biocompatible material having a lateral side, a medial side, a proximal end and an angled distal end, wherein at least one mechanical property of the implant is different on the lateral side than on the medial side. The mechanical property may be stiffness. In an alternate embodiment, the implant may include one or more different materials on the lateral side than on the medial side.

In yet another embodiment, the implant may be made of absorbable material that has a first density on the lateral side, and a second, different density on the medial side. The absorbable material may be an absorbable mesh and/or may further include a plurality of holes therethrough on the medial side.

Also provided is an implant for repositioning a patient's eyebrow that includes a substantially flat strip of biocompatible material having a proximal end, a distal end, and lateral and medial sides. The implant is non-symmetrical in that it is adapted, when the distal end is fixedly secured to a patient's tissue at a plurality of points along its length and when a pulling force is applied to the proximal end, to provide a gradient lift of the patient's tissue along the length of the distal end of the implant.

In one embodiment, the implant is geometrically non-symmetrical. In yet another embodiment, the implant further includes a foot portion that includes the distal end, and a vertical strip portion extending outwardly from the foot portion. The longitudinal axis of the vertical strip portion is offset from the center of the length of the foot portion.

In yet another embodiment, an obtuse angle is formed at the point of intersection of the longitudinal axes of the foot portion and vertical strip portion. This obtuse angle may be between 105 and 125 degrees.

The implant may have non-symmetrical mechanical properties, and in one embodiment may have a stiffness that is different on the lateral side than on the medial side.

In another embodiment, the implant includes one or more different materials on the lateral side than on the medial side.

The implant may further be made of an absorbable material that has a first density on the lateral side, and a second, different density on the medial side. The absorbable material may further be an absorbable mesh.

In yet another embodiment, the implant is made of an absorbable material having a plurality of holes therethrough on the medial side.

These and other features and advantages of the present invention will become apparent from the following more detailed description, when taken in conjunction with the accompanying drawings which illustrate, by way of example, the principles of the invention.

BRIEF DESCRIPTION OF THE DRAWINGS

FIGS. 3a-3d illustrate various steps in a method for implanting the implant of FIG. 2a.

FIGS. 4a-4b illustrate relative positioning of the implant of FIG. 2a before and after tension is applied to lift the brow of a patient.

DETAILED DESCRIPTION OF THE INVENTION

Before explaining the present invention in detail, it should be noted that the invention is not limited in its application or use to the details of construction and arrangement of parts illustrated in the accompanying drawings and description. The illustrative embodiments of the invention may be implemented or incorporated in other embodiments, variations and modifications, and may be practiced or carried out in various ways.

Figure 1:
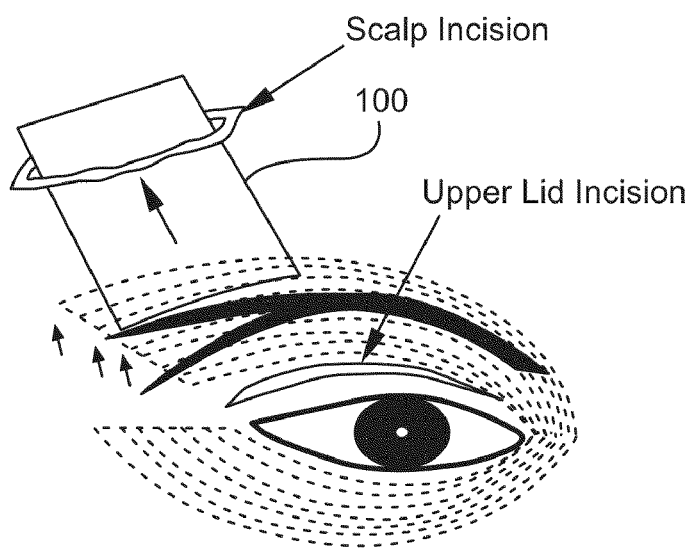
FIGS. 1 and 1a illustrate a known prior art brow lift implant and procedure.
Figure 1A:
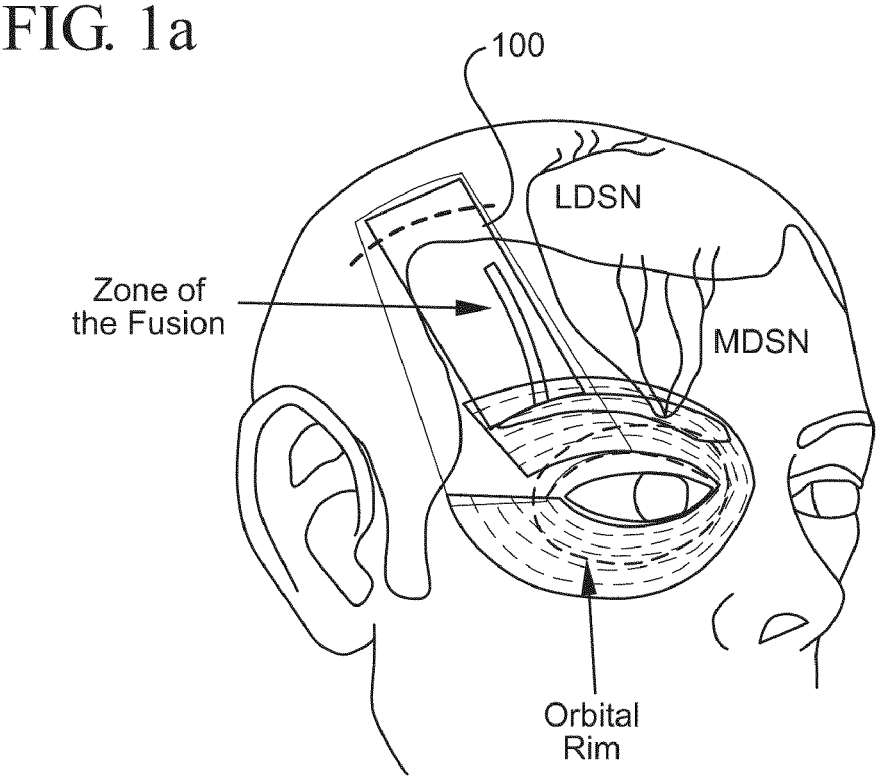
Figure 2A:
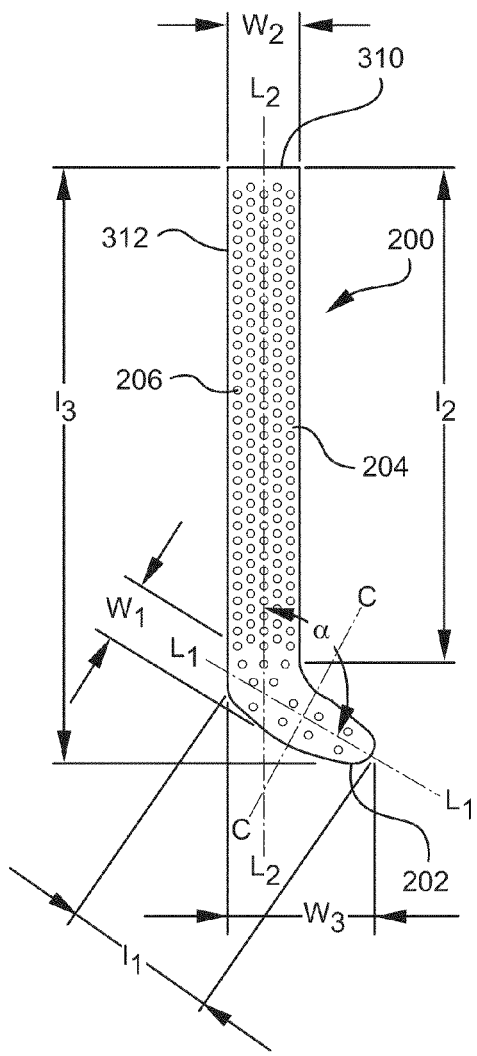
FIGS. 2a-2c illustrate an exemplary implant according to the present invention.
Figure 2B:
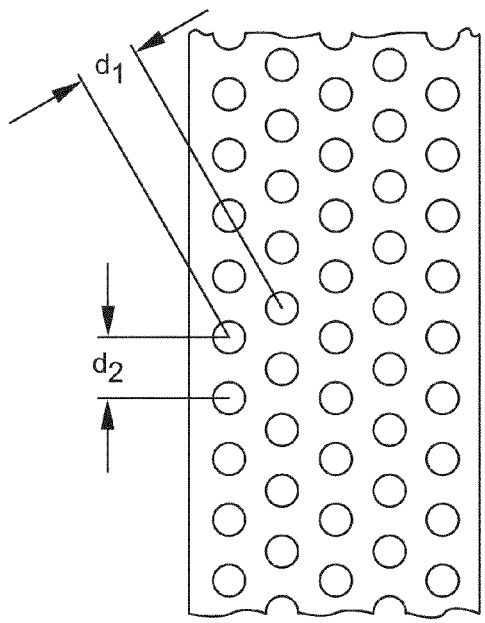
Figure 2C:
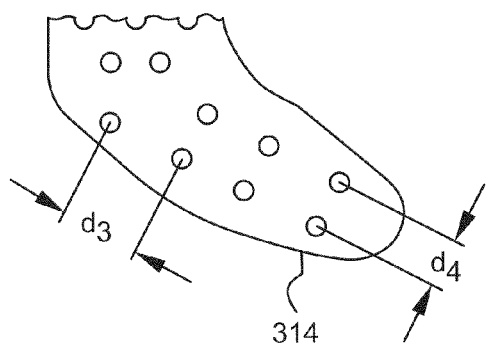

FIGS. 2a-2c illustrate an exemplary implant for brow lift procedures according to the present invention. The implant 200 includes a distal end portion or "foot" portion 202, and a vertical strip portion 204. The distal end portion extends along a first longitudinal axis $L_1$, whereas the vertical strip portion extends along a second longitudinal axis $L_2$. As can be seen in FIG. 2a, the first and second longitudinal axes $L_1$, $L_2$ intersect at an obtuse angle α. Further, the longitudinal axis $L_2$ is also offset from the centerline C-C ("offset" as used herein) that bisects the length $l_1$ of the foot portion, which in the illustrated embodiment is approximately 27.5 mm. The length $l_2$ and width $w_2$ of the vertical strip portion 204 are approximately 82 mm and 12 mm respectively, and the width $w_1$ of the foot portion 202 is approximately 10 mm. The overall length $l_3$ and width $w_3$ of this embodiment of the implant is approximately 100 and 24.8 mm respectively. As will be described further below, the obtuse angle and offset nature of the implant enable the implant of the present invention to provide a gradient lift along the brow through a one vector pull by the surgeon. A "gradient lift" along the brow as the phrase is used herein, means that the amount of lifting of the brow is greater at the lateral brow than it is at the medial brow (portion closest to center of the forehead). A "one vector pull" as the phrase is used herein, means that the surgeon need only place tension on the implant from substantially a single point.

In one embodiment, the implant 200 is fully absorbable and may be comprised of an absorbable mesh material such as Vicryl® mesh, which is manufactured by Ethicon, Inc. of Somerville, N.J. In a preferred embodiment, the implant is further laminated with a 50 μm polydioxanone (PDS) film. It is also preferable to further laminate the foot portion 202 with an additional 100 μm PDS film to enhance stiffness to allow better tension distribution when the strip is being pulled as will be described further below. Increased stiffness of the foot portion ensures better stress distribution across the entire span of the foot portion resulting in a smooth brow lift, and will also prevent buckling or distortion of the foot portion when the vertical strip portion is pulled by the surgeon.

The implant may have a plurality of holes 206 therethrough to facilitate tissue ingrowth. In the illustrated embodiment, the holes are approximately 1.5 mm in diameter and on the vertical strip portion 204 are placed along multiple parallel lines such that distances $d_1$ and $d_2$ are approximately 2.5 mm. In the illustrated embodiment, holes are placed through the foot portion such that distances $d_3$ and $d_4$ are approximately 5.5 and 3.5 mm respectively.

Figure 3A:
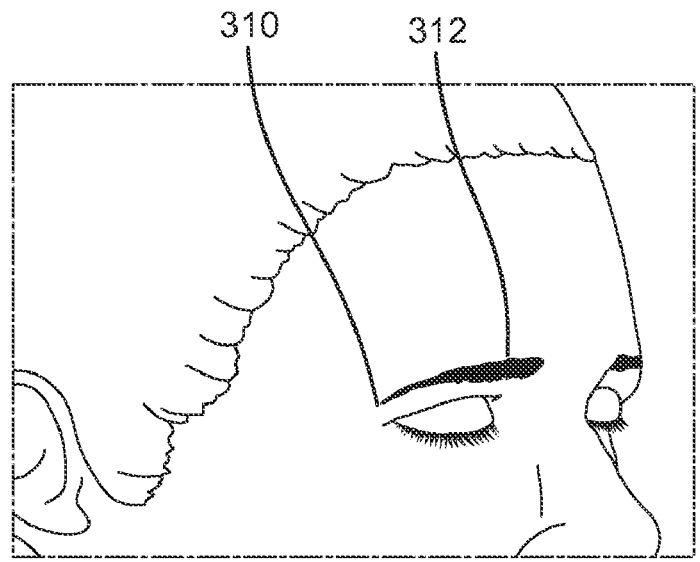
Figure 3B:
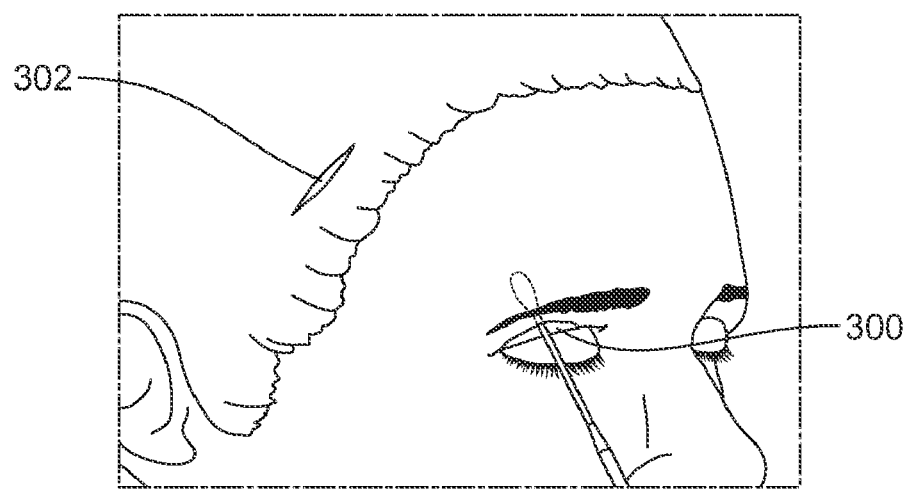
Figure 3C:
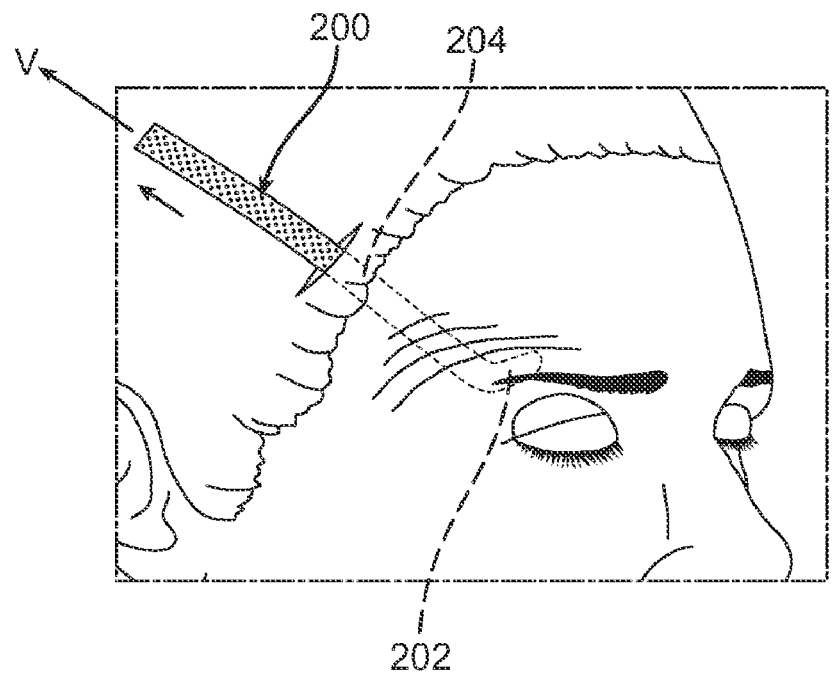
Figure 3D:

With reference now to FIGS. 3a-3d, where FIGS. 3a and 3d illustrate a patient before and after implantation surgery, placement of the implant of FIG. 2a will now be described in detail. The implant and the lateral brow lift procedure will be used in conjunction with the blepharoplasty where excess of the upper eyelid skin is removed to rejuvenate the eye. The implant is placed using two incisions, a first 300 along the upper eyelid as a part of blepharoplasty procedure and a second 302 superior to the frontal hairline in the temporal region as shown in FIG. 3b. The first incision 300 is a line above the eyelash line at the levels of the medial canthus, mid-pupil, and lateral canthus, respectively. The lower blade of forceps is placed over the line, and the excess upper eyelid skin is "pinched" to absorb the excess. The elliptical area of excess upper eyelid skin is then marked. The lateral forehead skin is then pushed up with a finger to locate the single vector line V along which the lateral eyebrow will be raised. This single vector line V preferably falls along the lateral side of the temporal fusion line of the skull vertically across the lateral forehead as shown in FIG. 3c. Then, about 2 cm superior to the frontal hairline, a 1-2 cm line is drawn perpendicular to the vector line.

The excess lower eyelid skin is then excised with the known blepharoplasty procedure, and dissection is performed approximately 2 cm upwardly from the first incision. The second incision 302 is then made at the location described above, and dissection is taken down through the superficial temporal fascia to the level of the deep temporal fascia. The superficial temporal fascia is then separated from the deep temporal fascia, with the dissection between these fascial planes stopping at the orbicularis temporal ligament. Then, the eyelid incision 300 is again used to raise the superficial temporal fascia from its adhesion to the lateral orbital rim and release it from the bone.

A periosteal elevator is used to raise periosteum over the entire frontal bone allowing this space to communicate with the subperiosteal space previously created through the upper eyelid or first incision 300.

The implant 200 is then introduced through the upper eyelid incision and passed under the periosteum, and a suitable instrument is used to pull the vertical strip portion up through the temporal scalp incision. The foot portion 202 of the implant is positioned under the eyebrow and is fixated with suture stitches to the suborbicularis fascia under the eyebrow. The holes 206 in the foot portion may be used as suture points. The vertical strip portion 204 is centered on a point just medial to the junction of the middle and lateral thirds of the eyebrow. The proximal end 310 of the vertical strip portion should be positioned just lateral to the temporal fusion line of the skull, and under the periosteum lining of the elevated forehead flap. The upper portion 312 of the vertical strip portion crosses the temporal fusion line of the skull to extend over deep temporal fascia as illustrated in FIG. 3c. The surgeon then pulls the implant 200 in the direction of the arrow of FIG. 3c to raise the brow to a desired level.

As indicated previously, as the foot portion 202 of the implant is secured across the brow by several stitches along its length or across its distal end 314, and as the vertical strip portion 204 is offset relative to the foot portion. When the surgeon pulls the implant along the single vector illustrated in FIG. 3c, the foot portion of the implant rotates slightly relative to the vertical strip portion, and thus the lateral side of the implant (and thus the lateral side 320 of the brow) is lifted more than the medial side 322 of the implant and brow. This rotation is illustrated in FIGS. 4a-4b, where FIG. 4a exemplifies the position of the implant 200 following suturing of the foot portion, but prior to placing tension on the vertical strip portion to raise the brow, and FIG. 4b illustrates the position of the implant after raising the brow to a suitable position. As illustrated, a gradient lift is achieved along the length of the brow from lateral 320 to medial 322 sides. In other words, the lift is concentrated at the lateral portion of the brow, and gradually decreases toward the medial portion of the brow. Referring back to FIG. 2a, to achieve this gradient the angle $\alpha$ is obtuse, and preferably between approximately 105 and 125 degrees, and more preferably approximately 117 degrees.

In the preferred embodiment described above, the gradient lift is achieved by the non-symmetrical geometry of having the longitudinal axis $L_2$ of the vertical strip portion offset from the centerline C-C of the longitudinal axis $L_1$ of the foot portion as described above. The gradient lift, however, can also be achieved by other means, such as by utilizing one or more non-uniform or non-symmetrical mechanical properties across the implant. For example, non-uniform mechanical properties, especially stiffness, can be achieved by using mesh or other material with different woven patterns, different thicknesses (with one material or more than one material), different materials, preferential reinforcement, different porosities across the width of the device, or any suitable combination. For example, an implant may be constructed having additional reinforcement on the lateral side (i.e., side placed nearest the lateral side of the brow).

Figure 5:
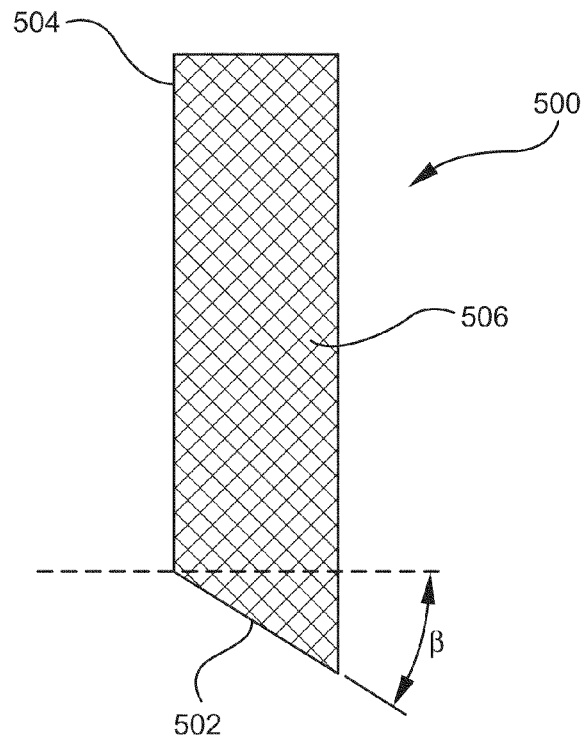
FIGS. 5 and 6 illustrate alternate embodiments of the present invention.
Figure 6:
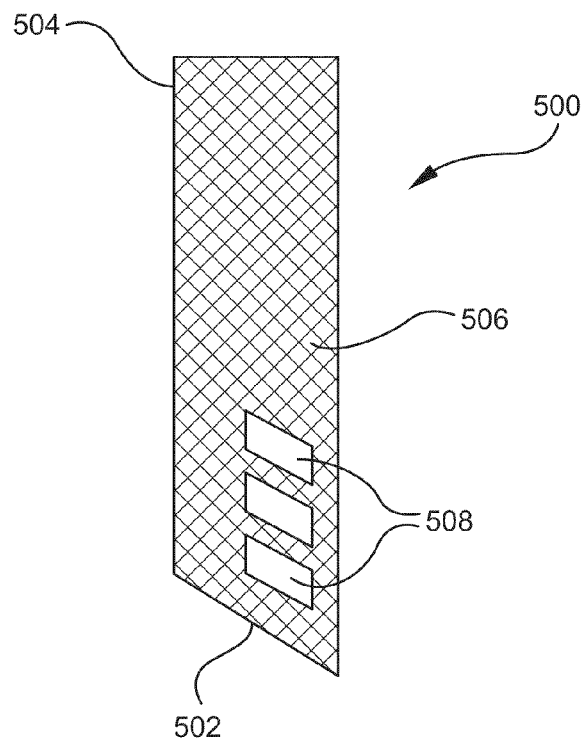

One example illustrated in FIG. 5 is an implant 500 comprised of a substantially rectangular strip with an angled distal end 502 having an angle $\beta$ of approximately 25 degrees. The implant is comprised of an absorbable Vicryl® mesh that is laminated with a 20 μm PDS film, and an additional 100 μm PDS film on the lateral portion 504 of the implant as opposed to the medial portion 506. Non-uniform stiffness may also be achieved across a mesh implant that is laminated with a PDS film by providing additional embroidery on the implant at predetermined locations, such as on the lateral side of the device. Thus, the implant is "non-symmetric" in terms of mechanical properties. Other means for creating non-symmetrical mechanical properties include varying porosity of the material from lateral to medial sides (lower porosity on the medial portion), varying a pattern of holes through the implant to achieve such a result, or using a mesh having different woven patterns from lateral to medial sides. FIG. 6 illustrates another embodiment according to the present invention comprised of a substantially uniform material or materials throughout, but having a plurality of apertures 508 placed through the medial portion 506 to achieve non-symmetrical mechanical properties from medial to lateral as described above.

While the foregoing describes specific embodiments of the present invention, other and further embodiments may be devised without departing from the basic scope thereof. As such, the scope of the present invention is to be limited only as set forth in the appended claims.

What is claimed is:

1. An implant for repositioning a patient's eyebrow, comprising:
   a foot portion adapted to be positioned along at least a portion of a length of a patient's eyebrow, the entire foot portion extending along a single, first longitudinal axis and having a length;
   a vertical strip portion extending outwardly from a first side of the foot portion to a distal end and adapted to extend upwardly across at least a portion of the patient's forehead, the entire vertical strip portion extending along a single, second central longitudinal axis and having a length, and a width extending between an outer lateral edge and an inner lateral edge, wherein the width is smaller than the length of the foot, wherein the second central longitudinal axis bisects the width of the vertical strip portion along an entirely of its length, wherein no portion of the foot portion extends outwardly beyond the outer lateral edge of the vertical strip portion, and wherein the foot portion is non-symmetric about the second central longitudinal axis,
   wherein the second longitudinal axis is offset from a center of the length of the foot portion and is at an obtuse angle relative to the first longitudinal axis such that a pulling force applied to the distal end of the vertical strip portion is entirely distributed along a length of the foot portion in a gradient manner that decreases along the length from the first side to the distal end, and wherein the implant is substantially flat having first and second opposing surfaces having no protrusions extending outwardly therefrom.

2. The implant according to claim 1, wherein the first and second longitudinal axes form an obtuse angle therebetween at a point of intersection.

3. The implant according to claim 2, wherein the obtuse angle is greater than 105 degrees.

4. The implant according to claim 3, wherein the obtuse angle is between 105 and 125 degrees.

5. The implant according to claim 1, wherein the implant is comprised entirely of an absorbable material or materials.

6. The implant according to claim 5, wherein the implant is comprised of an absorbable mesh.

7. The implant according to claim 6, wherein the implant further comprises an absorbable film on said first and/or second surfaces.

8. The implant according to claim 7, wherein the film is a polydioxanone film.

9. The implant according to claim 8, wherein the polydioxanone film has a thickness of approximately 20-200 μm.

10. The implant according to claim 8, wherein the polydioxanone film has a thickness of approximately 50 μm on the vertical strip portion, and a thickness of approximately 150 μm on the foot portion.

11. The implant according to claim 7, further comprising a plurality of holes therethrough.

* * * * *